United States Patent [19]
Taylor

[11] Patent Number: 5,275,789
[45] Date of Patent: Jan. 4, 1994

[54] APPARATUS FOR IODINATION/PURIFICATION

[75] Inventor: William R. Taylor, Lowell, Mass.

[73] Assignee: E. I. Du Pont de Nemours and Company, Wilmington, Del.

[21] Appl. No.: 899,898

[22] Filed: Jun. 17, 1992

Related U.S. Application Data

[62] Division of Ser. No. 623,261, Dec. 5, 1990, Pat. No. 5,206,346.

[51] Int. Cl.$^5$ .................................. G21C 1/00
[52] U.S. Cl. .................................. 422/159; 422/903; 436/541; 436/542
[58] Field of Search .................. 422/159, 149, 903, 70, 422/71; 436/541, 542; 424/1.1; 530/391.3; 534/10, 11

[56] References Cited

U.S. PATENT DOCUMENTS

| | | | |
|---|---|---|---|
| 3,561,932 | 2/1971 | Gruverman et al. | 422/159 |
| 3,774,036 | 11/1973 | Gerhart | 422/159 |
| 3,970,583 | 7/1976 | Panek-Finda | 422/159 |
| 4,425,438 | 1/1984 | Bauman et al. | 436/542 |
| 4,775,638 | 10/1988 | Haisma | 436/547 |
| 4,782,231 | 11/1988 | Svoboda et al. | 422/159 |
| 4,996,856 | 10/1990 | Ito et al. | 436/170 |

OTHER PUBLICATIONS

Ferens et al., "High Level Iodination of Monoclonal Antibody Fragments for Radiotherapy" J. Nucl. Med. vol. 25, No. 3 367-370 (1984).

James et al., "A Shielded, Sterile Apparatus for Iodinating Proteins" Med. Lab. Sci. vol. 40, 67-68 (1983).

Henville et al., "A Simple Cheap Remotely Operated System for the Iodination of Proteins" Anal. Biochem vol. 52 336-341 (1973).

Weadock et al., "A Simple Remote System for the High Level Radio-Iodination of Monoclonal Antibodies" J. Nucl. Med. All. Sci. vol. 40 37-41 (1989).

Primary Examiner—Robert J. Warden
Assistant Examiner—Hien Tran

[57] ABSTRACT

Materials are labelled with a radioisotope by passing them through a column packed with (a) beads coated with an oxidizing reagent for coupling the radioisotopes to the materials, (b) as anion resin, and (c) a material for trapping elemental isotope, and flowing a mixture of the radioisotope and a solution of the material to be labelled through the column.

5 Claims, 2 Drawing Sheets

APPARATUS FOR IODINATION/PURIFICATION

This is a division of application Ser. No. 07/623,261, filed Dec. 5, 1990 now U.S. Pat. No. 5,206,346.

FIELD OF THE INVENTION

The present invention relates to the preparation and use of molecules carrying attached thereon radiolabeled species.

DESCRIPTION OF THE PRIOR ART

The use of radiolabeled therapeutic and diagnostic agents has recently received renewed interest. The development of monoclonal antibodies of high avidity and specificity has encouraged the development of new agents for diagnostic and therapeutic treatment of cancer. These radiolabeled monoclonal antibodies, ligands, unsaturated fatty acids and other compounds are finding clinical applications both in vitro (for example in radioimmunoassay systems) and in vivo (for example in diagnostic imaging, radiotherapy and other novel techniques such as radioimmunoguided surgery).

Bifunctional chelates are being utilized to radiolabel the above mentioned biomolecules, e.g., antibodies and other agents with $Y^{90}$, $In^{111}$, $Re^{186}$, $Ga^{67}$ etc., for diagnostic and therapeutic purpose, however, $I^{125}$, $I^{131}$ and $I^{123}$ remain the radioisotopes of choice for use with the method and apparatus of this invention.

Several remote or semiautomatic radiolabelling, specifically radioiodination, systems have been described (see for example, Ferens J. M., Krohn K. A., Beaumier P. L. et al., High-level iodination of monoclonal antibody fragments for radiotherapy. J Nucl Med 1984;25:367-70; or James S. F. W., Fairweather D. S. L., Bradwell A. R., A shielded sterile apparatus for iodinating proteins, Med Lab Sci 1983;40:67-8; or Henville A. Jenkin G., A simple and cheap remotely operated system for the iodination of proteins, Anal Biochem 1973;52:336-41). These systems are dependent on gel filtration columns to separate bound from free isotope and in line pumps to propel reagents from one vessel to another. Such systems are prone to leakage, difficult to shield, and require decontamination after use.

Other shieldable, disposable and relatively cheap systems are reported (see for example, Weadock K. S., Anderson L. L., Kassis A. I., A simple remote system for the high-level radioiodination of monoclonal antibodies; J Nuc Med All Sci 1989;33:37-41, or James Watson S. F., Fairweather D. S., Bradwell A. R., A shielded, sterile apparatus for iodinating proteins, Med Lab Sci 1983;40:67-68.) but these systems are complex to use requiring manipulation of valves and positioning of needles. These systems are inherently less reliable for iodinating since the result will depend on the mechanics of vial coating and the timing of the iodination and purification reactions. These systems are also more difficult to shield than the present invention because there are multiple vials to shield (apparatus is spread out) and a lead wall is also required.

Another technique is the 'single vial technique' described in U.S. Pat. No. 4,775,638. This technique, although simple looking, requires manipulations of reagents with a syringe, and the timing of incubations. The mechanics of vial coating with the iodination reagent, manipulation of reagents and timing of the reaction, contribute to reduced consistency of results. Also, it would be difficult to safely shield the user from the radiation field emanating from the syringe utilized in this method, especially when preparing therapeutic doses of $I^{131}$ labeled agents.

A similar technique to the 'single vial technique' described above is the Iodo-Bead TM method of Pierce Chemical. This method is essentially identical to the 'single vial technique' except that instead of coating the reaction vial with oxidant, one or more Iodo-Beads TM are added to the reaction vial. The same concerns for reagent manipulation, timing of incubation and shielding apply to this technique. In addition, the Iodo-Bead TM has a polystyrene base which will absorb oxidized iodine from the reaction mixture and thus reduce the percent incorporation of iodine into the agent of interest.

Radioiodinated monoclonal antibodies and other radiolabelled compounds may soon serve as standard diagnostic and therapeutic tools in clinical oncology. When preparing these agents, the integrity of the agent must be maintained while minimizing personnel exposure to radioactivity, including direct exposure to radiation and internal exposure to the thyroid. Thyroid uptake of radioiodine can easily result if elemental radioiodine generated in the labeling process is not contained. The ability to prepare these agents in a consistent manner, including specific activity, yield and purity will be useful in evaluating potential therapies. Simplification of the radiolabeling process will allow widespread use of the new therapies as they become available.

SUMMARY OF THE INVENTION

Many of the disadvantages of the prior art methods and apparatus are alleviated by this invention. According to the invention, a method of labelling materials with a radioisotope comprises the steps of providing a sealed column having an inlet end and an outlet end, the column being packed with sequential stages of (a) beads coated with an oxidizing reagent for coupling the radioisotopes to the biomolecule, (b) an anion exchange resin, and (c) a material for trapping elemental radioisotope, and flowing a mixture of the radioisotope and a solution of the material to be labelled through the column, and collecting the purified product at the effluent side of the device. The radiolabeling reaction (incorporation of radiolabel into the functional material) and the purification reaction (removal of unincorporated radiolabel from the radiolabeled material) occur as the reaction mixture flows through the column. In addition, all unincorporated radiolabel is contained and trapped within the column, thus, reducing the quantity of radioactive waste generated and eliminating the need to handle this waste. In a preferred embodiment of the invention, the mixture is flowed through a device, typically a column, as described.

This method is particularly suited for labeling monoclonal and polyclonal antibodies for use in radioimmunoguided surgery, radiotherapy and diagnostic imaging. Consistent radiolabeled antibody yields and purity are obtained when utilizing this method without releasing volatile radioiodine. Higher yields of radiolabeled antibody are obtained when using the device compared to other methods. The apparatus used in the method is easily shielded and can be operated remotely if a pump such as a peristaltic pump is utilized to flow the reaction mixture through the column. Radiolabeling by this method is rapid and easy and does not generate radioactive waste except for that contained within the device itself.

The invention also includes an apparatus for labelling materials with a radioisotope comprising a sealed column having an inlet and an outlet, the column being packed with, in the order named, (a) beads coated with an oxidizing reagent for coupling the radioisotope to the material, (b) an anion resin, and (c) a material for trapping elemental radioisotope, whereby when a radioisotope and a buffer solution of the material are passed through the column, the radioisotope becomes reactively coupled to the material. In a preferred embodiment of the invention, the beads of (a) are coated with an iodination reagent. Further the material for trapping elemental radioisotope is chloromethylated styrene resin. Additional material for trapping elemental isotope may be placed at the inlet end of the column. Finally, filters may be placed at the inlet ends and outlet ends of the column between beads (a) and (b).

This particular apparatus has many advantages over similar devices of the prior art. For one, the higher surface area of the glass beads coated with an oxidizing agent enhances the reaction kinetics of the operation. The apparatus permits a more efficient conversion of the radiolabel to labelled materials. Virtually all the radioactivity is contained in one vessel and requires no valves or connectors. After use, the ends of the apparatus can be sealed and its entire contents remain self-contained for safe disposal. Exposure of the operator's hands to the radioactivity is not significant. The approaches of the prior art require significant hand manipulation of syringes or bottles thus making the possibility of radiation exposure to the hand a real concern. Finally, the apparatus of the invention permits higher specific activity of the labelled materials.

BRIEF DESCRIPTION OF THE DRAWINGS

The invention may be more fully understood from the following detailed description thereof taken in connection with the accompanying drawings which form a part of this application and in which.

DESCRIPTION OF THE PREFERRED EMBODIMENT

Figure 1:
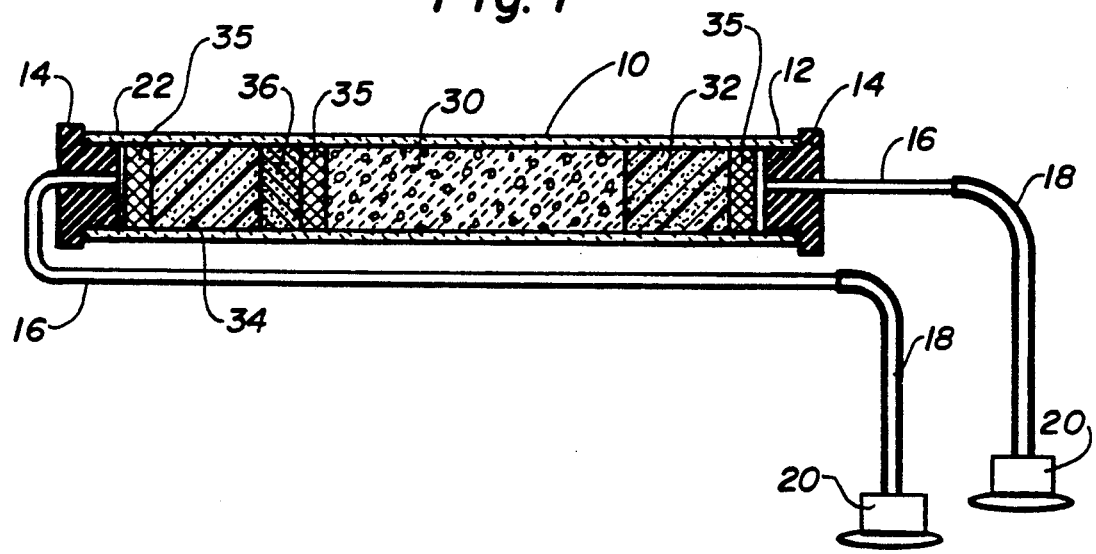
FIG. 1 is a cross-sectional view of a column for labelling materials with a radioisotope constructed in accordance with a preferred embodiment of this invention.

The apparatus of this invention may be best seen in FIG. 1 in which a column 10 is depicted. The column has an inlet end 12 provided with an end plug 14 from which is connected a stainless steel tubing 16 thence through silicone tubing 18 to a Luer adaptor with IV sites 20. The column also has an outlet end 22 which is provided with an end plugs 14 which is connected through stainless steel tubing 16 thence silicone tubing 18 to a Luer adaptor 20.

The interior of the column is packed with glass beads 30 coated with a mild oxidizing agent as will be described. Positioned upstream from the glass beads 30 is a chloromethylated styrene resin 34, a polyethylene frit filter 35 and an end plug 14.

Positioned downstream from the glass beads is another filter 35 and an anion resin 36, chloromethylated styrene resin 34, a third filter 35, and an end plug 14.

The apparatus of this invention may be used in a flow system depicted in FIG. 2 in which the column 10 receives a reaction mixture, as will be described, from the supply source 40, which is coupled by silicone tubing 42 through a peristaltic pump 44, through the column 10, and a filter 46, thence to a collection vial 48.

The apparatus contains a bed of glass beads 30 which have been uniformly coated with an oxidizing agent for coupling the radioisotope to a material. While many radioisotopes as will be described may be used, the invention will be described for simplicity in the context of the iodination of an antibody. For the iodination of antibody, the preferred oxidant is Iodogen. Iodogen is a mild oxidizing agent (formula 1,3,4,6-Tetrachloro-3,6-diphenyl glycoluril) which is insoluble in water. The use of this mild oxidant for coupling limits the chemical damage done to functional agents in the iodination process.

A thin layer of iodogen (available from Pierce Chemical) is coated onto the beads using the chloroform solvent evaporation technique recommended by Pierce. This Iodogen coating does not wash off the beads when they are utilized as intended in the present invention, which is to serve as a mild oxidizing agent for the oxidation of iodide ion, and also by virtue of the large surface area of the glass beads, to expose the reaction mixture to a large oxidizing surface with which to react and thus dramatically increase the kinetics of the reaction involving the oxidation of iodide ion.

In the preferred embodiment, the iodogen coated glass beads 30 are ~100 microns in diameter as utilized in the device for iodinating mono or polyclonal antibodies or their fragments. The size of the glass beads used in the device determines the total iodogen surface area to which the functional agent is exposed during the coupling reaction. The total exposed iodogen surface area in turn determines the rate of reaction (kinetics) of the coupling reaction. In the preferred embodiment, a glass bead size has been chosen which provides a sufficiently rapid reaction rate that, the reaction mixture can be rapidly flowed through the device at 1 ml per minute, and the flow rate can be increase or decreased ten fold, 0.1 ml per minute to 10 ml per minute, without effecting the yield (% coupling) from the device. In this way the consistency of results from the device is enhanced.

In some instances the optimum glass bead diameter may be larger or smaller than 100 microns depending on the geometry of the device which in no way is restricted by this description, or by the physical or chemical properties of the functional agent of interest in the reaction mixture.

Iodogen has been found to adhere well to glass beads, however, any material may be substituted for glass provided that the iodinating agent used adheres to the material and does not wash through into the radioiodinated product and that the material does not react with oxidized iodine, thus removing iodine from the reaction mixture. The geometry of the beads need not be spherical, and non-porous as well as very highly porous materials can be used to enhance the available surface area, however, the surface area of the carrier of the iodination reagent (oxidant) must be well known in order that the appropriate quantity of oxidant can be deposited thereon.

The chemical agent coated onto the glass beads is not restricted to iodogen but can be any mild oxidizer which can be made to be insoluble in water by any method, either before or after the coating process. Other mild oxidizers which may be used include chloramine T, Lactoperoxidase and iodine monochloride, for example.

The quantity of iodogen coated glass beads 10 utilized in the device will depend on the desired yield or iodine incorporation, geometry of the device and chemical and physical properties of the reacting functional agent as stated above.

In the preferred embodiment, the apparatus contains an anion resin 36 through which the reaction mixture passes after passing through the iodogen coated glass beads. The anion resin 36 removes and traps $I^-$, $IO^-$, $IO_3^-$, $IO_4^-$, or other negatively charged iodine species thus effecting a purification of the radioiodinated functional agent. The preferred anion resin is Biorad Labs AG1X8 which has a high affinity for these iodine species.

Other materials or methods such as gel filtration media, organic or inorganic ion exchangers, other methods for size exclusion chromatography, etc., which are well known in the art may be utilized in the device to effect a purification of the reaction product.

The apparatus contains a bed of chloromethylated polystyrene resin 34 through which the reaction product passes after passing through the iodogen coated glass beads 30 and the anion resin 36. This chloromethylated polystyrene resin 34 absorbs and traps $I_2$, $ICl$, $I^+$ or any other oxidized iodide species which may remain in the reaction product, thus effecting an additional purification step. There is enough resin present in this resin bed to absorb and trap any oxidized iodide present as an impurity in the reaction product as well as any amount of oxidized iodide that might be generated if all the iodide present on the anion resin previously described were oxidized. In this way, all radioiodine species are contained and trapped within the device.

Other materials such as TEDA (Triethylenediamine), charcoal, any styrene based resins, or other materials well known in the art to absorb and trap oxidized iodide may be utilized in the device as a substitute for any chloromethylated styrene resins utilized in the preferred embodiment of this invention.

The chloromethylated styrene resin bed described above has an additional function when the device is used to radioiodinate functional agents, which is to trap volatile radioiodine species that may be generated within the device at some time after the device has been used for the intended purpose. There is an additional, identical chloromethylated styrene resin 34 on the inlet side of the device, adjacent to the iodogen coated glass beads 30. In this way, there is a chloromethylated styrene resin bed at each end of the column which will absorb and trap any volatile oxidized radioiodine species which may be generated at some time after the use of the column. This renders the column free from radioactivity release to the environment.

BEST MODE FOR CARRYING OUT THE INVENTION

Figure 2:
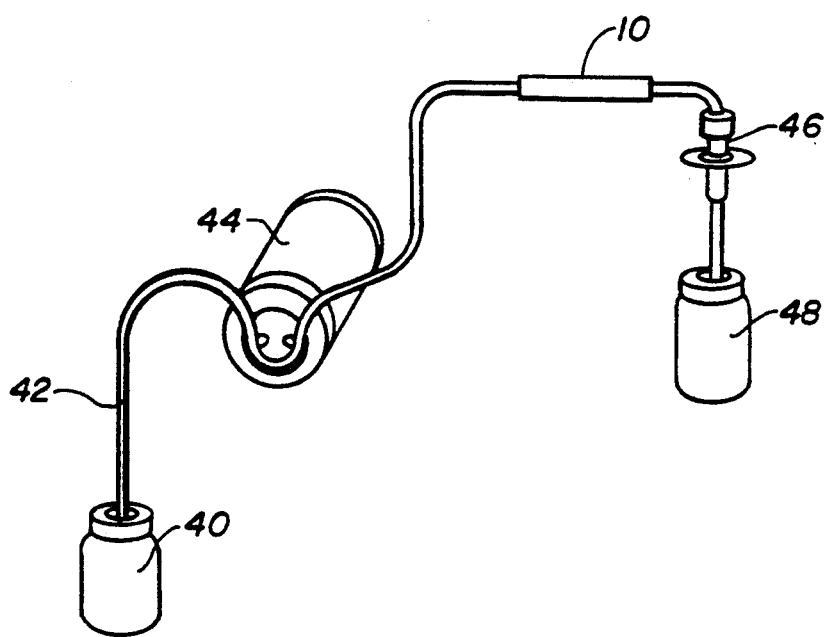
FIG. 2 is a system in which the apparatus of FIG. 1 may be used for labelling materials with radioisotopes.

The radiolabeling procedure is performed by passing the reaction mixture through the device and collecting the eluant using the system of FIG. 2. The apparatus is composed of a cylindrical column, 2.75 inches long by 0.375 inches in diameter, containing the oxidant adjacent to an anion resin 36 with a chloromethyl styrene plug 14 at each end. The column can be glass or plastic. The column contains three polyethylene frit filters 35 having a pore size opening of ~70 microns. These frit filters 35 are placed within the glass column 10, one at each end and one separating the glass beads 30 from the anion resin 36. The frit filter 35 on the inlet side ensures the even application of the reaction mixture onto the device. The frit filter 35 between the glass beads 30 and the anion resin 36 eliminates mixing of these two components which could potentially generate oxidized iodine in used devices. The frit filter 35 on the outlet side prevents resin particles from entering the purified product. Frit filters 35 can be constructed of any inert material. The pore size of the frit filters 35 must be smaller than the resin particle size.

The column has a means for introduction of the reaction mixture and elution of the purified product under sterile or semi-sterile conditions. In the preferred embodiment, the envelope of the column is a glass cylinder sealed at each end by a silicone rubber plug 14 which is penetrated by stainless steel tubing 16. Silicone rubber inlet and outlet tubings 18 are connected to the stainless steel tubings 16. The ends of the silicon tubings are fitted with Luer adapters 20 with IV sites (Medex Corp.). In this way the device is sealed but accessible by piercing the IV sites on the inlet and outlet side of the device with a needle.

To utilize the apparatus in a sterile condition, the device can be opened by removing the Luer adapters with IV sites and sterilized by the ethylene oxide technique. When the Luer adapters are reassembled using aseptic technique, the device becomes a sealed sterile unit.

The radiolabeling reaction is initiated by flowing the mixture (from container 40) of monoclonal antibody and radiolabel through the apparatus. In the preferred embodiment, the reaction mixture is pumped onto the device with a peristaltic pump 44 (FIG. 2) by piercing the IV site on the inlet side of the device with a needle connected to the outlet side of the pump tubing. The purified product is collected from the outlet side of the apparatus in the collection vial 48.

A syringe or other method could be used to introduce the reaction mixture to the device. The reaction mixture is added in a buffered solution, preferably phosphate buffered saline at pH 7-7.5. For other proteins and molecules the optimum buffer parameters may be different but can be determined experimentally.

The radioiodine can be $^{125}I$, $^{123}I$ or $^{131}I$ available commercially as NaI in NaOH, preferably at a pH of 8-10. The radioiodine should be premixed with the monoclonal antibody and buffer solution before introduction to the device.

When iodinating monoclonal antibodies, the reaction mixture is introduced to the device at a flow rate ~1 ml per minute. The flow rate can range from ~0.1 ml to 10 ml per minute at room temperature without adversely effecting the yield and purity of the product. When iodinating other proteins or compounds the optimum flow rate may be different but can be determined by experiment.

After the reaction mixture has been pumped onto the apparatus, the pump 44 is allowed to continue pumping until no more reaction product is eluting from the apparatus. In this way, the device is pumped dry or semidry. The apparatus is then rinsed by pumping 1 ml of the same buffer used to dilute the reaction mixture through the apparatus. The rinse, which contains ~20% of the product can be collected together with the first elution of product.

In the preferred embodiment, this method is used to iodinate monoclonal and polyclonal antibodies, however, the device can be used to radioiodinate any iodinatable species including any protein, any organic compound or biomolecule containing an activated phenyl group, i.e., a phenyl group with an electron donating group attached (examples of which include, —OH, —NH$_2$, —NHR, —NR$_2$), any organic compound or biomolecule containing heterocyclic rings, i.e., certain histidyl moieties, any organic compound or biomolecule substituted with trimethylsilyl or tri n-butyl tin functional groups, tri n-butyl tin substituted phenyl groups not containing electron donating groups, any biomolecule containing tyrosine. Other species which can be radioiodinated via this method include steroids, fatty acids, peptides, proteins, hormones, enzymes, toxins, amino acids, and carbohydrates.

Although, in the preferred embodiment the method is used to iodinate antibodies, the method can be adapted to include its use in radiolabeling antibody with other isotopes such as $^{90}Y$, $^{111}In$, $^{186}Re$, $^{67}Ga$ and other radiometals.

The present invention is partly based on the discovery of a method to improve the reaction kinetics of the iodination reaction, this kinetic effect was not utilized in the prior art. The improved reaction kinetics result when a mild oxidizing agent is made available on a very large surface area within the small volume of the device to react with a monoclonal antibody/radioiodine mixture. The large oxidizing surface presented to the reaction mixture increases the probability for molecular collisions which result in radioiodination of the antibody. The increased rate of iodination embodied by the present invention allows the assemblage of oxidation and purification components into a small, flow through design for the iodination of functional agents which is also very easily shielded when radioiodines are used.

EXAMPLE 1

Radioiodination of a monoclonal antibody to colorectal cancer #17-1a (Centocor Corp.) was obtained as a 10 mg/ml solution in saline. $^{125}I$ was obtained from E. I. Du Pont de Nemours and Company, Billerica, Mass., Catalog No. NEZ033L as a high specific activity, reductant free solution of NaOH at a pH 8-10, at 4 mCi/ml, 17.4 Ci/mg.

Radioiodination was accomplished utilizing a modification of the iodogen (1,3,4,6 tetrachloro-3, 6-diphenylglycoluril) method, Fraker, P. J. and Speck, J. C. Biochem. Biophys. Res. Commun. 80: 849-857 (1978), utilizing the iodogen as a thin coating on glass beads, in a flow through design of FIG. 1. Labeling was performed by passing 4.0 ml of the antibody/radiolabel mixture through a device at a flow rate of 1 ml per minute and collecting the eluant.

A mixture containing 30 mg of F(ab')2 fragment of monoclonal antibody 17-1A (Centoca Corp.) and 1.43 mCI of $^{125}I$ as sodium iodide was diluted to a total volume of 4.0 ml with pH 7.4 phosphate buffered saline and pumped through the device at a flow rate of 1.2 ml/min. The eluant was collected and assayed by capintec ion chamber. A second solution composed of 4.0 ml of pH 7.4 phosphate buffered saline was then pumped through the apparatus of FIG. 1 and the eluant collected and assayed by capintec ion chamber. A sample of the product collected from the first eluant collection was analyzed for purity by "instant TLC". The purity was 95% and the yield based on a combination of the two elutions was 89.9%.

Figure 3:
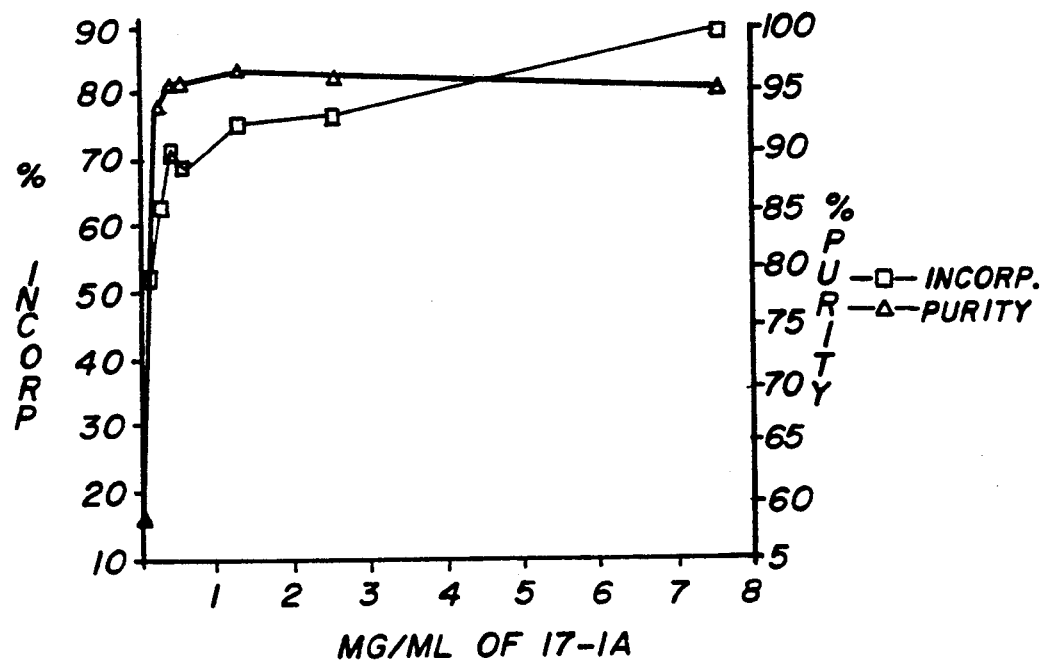
FIG. 3 is a graph depicting the results of radiolabelling of Mab 17-1A.

The degree of incorporation of $I^{125}$ into the 17-la monoclonal antibody was found to be a function of the antibody concentration in the reaction mixture. In the antibody concentration range examined, (0.125-7.5 mg/ml) the incorporation yield varied from ~50-90% and the product purity was ~95% as determined by "instant TLC". This data is shown in FIG. 3.

The radiochemical purity was determined by thin layer chromatography. A sample of the iodinated antibody was developed on a silica gel impregnated fiberglass "instant TLC" plate (Gelman Sciences). The developing solution is Normal Saline and the developed plate is read on an Auto Changer 3000 radiochromatogram scanner (Bioscan Inc., Washington, D.C.). The percent purity is calculated as the area under the peak of the radiation profile of the antibody divided by the area of the radiation profile of the TLC plate in its entirety.

EXAMPLE 2

Generic human IgG was obtained from Cooper Biomedical (Malvern, Pa.) as a lyophilized powder which was reconstituted in 50 mm PBS solution at pH 7-7.5. A reaction mixture was prepared as is described in Example 1 but this time including the generic human IgG and passed through the apparatus of FIGS. 1 and 2. More specifically, a mixture containing 50 mg of generic human IgG and 917 uCi of $^{125}I$ as sodium iodide was diluted to a total volume of 4.0 ml with pH 7.2 phosphate buffered saline. This solution was pumped through an apparatus prepared as stated above at a flow rate of 1.2 ml/min, and the eluant collected and assayed with a capintec ion chamber. A second solution composed of 4.0 ml of pH 7.2 phosphate buffered saline was then pumped through the apparatus and the eluant collected and assayed by capintec ion chamber.

Figure 4:
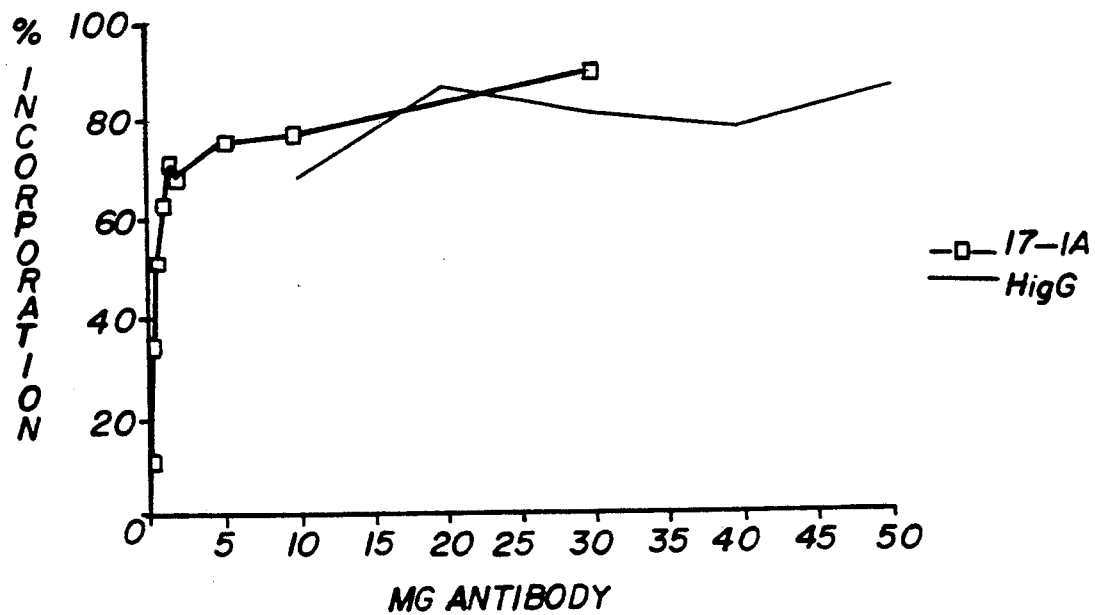
FIG. 4 is a graph depicting the results of radiolabelling human antibody utilizing the apparatus of this invention.

A sample of the product was collected from the first eluant collection vial 48 and analyzed for purity by "Instant TLC". The purity was 99% and the yield based on a combination of the two eluations was 86.8%. The results of this experiment are shown in FIG. 4.

I claim:

1. An apparatus for labelling iodinatable species with a radioisotope comprising:
    a sealed column having an inlet and an outlet, the column being packed with, in the order named, (a) bead mean having surface areas coated with an oxidizing reagent thereby causing the kinetics of a reaction for coupling a radioisotope to an iodinatable species to be accelerated due to presence of an extensive oxidizing surface, (b) an anion resin, and (c) means for trapping elemental radioisotope.

2. The apparatus of claim 1 wherein the means for trapping elemental radioisotope is chloromethylated styrene resin.

3. The apparatus of claim 1 wherein the column is also packed with chloromethylated styrene resin positioned inside the column adjacent to the inlet.

4. The apparatus of claim 1 wherein the column is provided with one filter positioned inside the column adjacent to the inlet and one filter positioned inside the column adjacent to the outlet and at least one filter between packings (a) and (b).

5. An apparatus for labelling iodinatable species with a radioisotope comprising:

a sealed column having an inlet and an outlet, the column being packed with, in the order named, (a) bead means having surface areas coated with an oxidizing and iodination reagent causing the kinetics of a reaction for coupling a radioisotope to an iodinatable species to be accelerated due to presence of an extensive oxidizing surface, (b) an anion resin, and (c) means for trapping elemental radioisotope.

* * * * *